United States Patent
Cook et al.

(10) Patent No.: US 10,544,197 B2
(45) Date of Patent: Jan. 28, 2020

(54) FGF-23 EPITOPE PEPTIDE FOR IMPROVING RESISTANCE TO BREAKAGE AND EGGSHELL STRENGTH

(71) Applicant: WISCONSIN ALUMNI RESEARCH FOUNDATION, Madison, WI (US)

(72) Inventors: Mark Eric Cook, Madison, WI (US); Zhouzheng Ren, Madison, WI (US); Alexis Jo Piepenburg, Reedsville, WI (US); Daniel Butz, Madison, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 113 days.

(21) Appl. No.: 15/675,022

(22) Filed: Aug. 11, 2017

(65) Prior Publication Data

US 2018/0044390 A1  Feb. 15, 2018

Related U.S. Application Data

(60) Provisional application No. 62/374,224, filed on Aug. 12, 2016.

(51) Int. Cl.
| | | |
|---|---|---|
| C07K 7/06 | (2006.01) | |
| C07K 14/50 | (2006.01) | |
| A61K 38/08 | (2019.01) | |
| A61K 38/18 | (2006.01) | |
| A61K 47/64 | (2017.01) | |
| A61K 39/385 | (2006.01) | |
| A61K 39/00 | (2006.01) | |

(52) U.S. Cl.
CPC .......... C07K 14/50 (2013.01); A61K 38/1825 (2013.01); A61K 39/385 (2013.01); A61K 47/64 (2017.08); A61K 2039/54 (2013.01); A61K 2039/552 (2013.01); A61K 2039/62 (2013.01)

(58) Field of Classification Search
None
See application file for complete search history.

(56) References Cited

U.S. PATENT DOCUMENTS

| | | | |
|---|---|---|---|
| 5,846,547 A * | 12/1998 | Cleary | A61K 39/092 424/244.1 |
| 9,078,842 B2 | 7/2015 | Cook et al. | |
| 2013/0183408 A1 | 7/2013 | Gurbuz et al. | |
| 2013/0331325 A1 * | 12/2013 | Mohammadi | C07K 14/50 514/9.1 |

OTHER PUBLICATIONS

Bobeck et al.; "Maternally-derived Antibody to Fibroblast Growth Factor-23 Reduced Dietary Phosphate Requirements in Growing Chicks"; Biochemical and Biophysical Research Communications; 420; pp. 666-670; (2012).

Ren et al.; "Antibody to Fibroblast Growth Factor 23-peptide Reduces Excreta Phosphorus of Laying Hens"; Poultry Science; 96; pp. 127-134; (2017).

Soares et al.; "Potential Role of 1,25 Dihydroxycholecalciferol in Egg Shell Calcification"; Poultry Science; 67; pp. 1322-1328; (1988).

\* cited by examiner

*Primary Examiner* — Christine J Saoud
(74) *Attorney, Agent, or Firm* — Cantor Colburn LLP

(57) ABSTRACT

Described herein are FGF-23 epitope peptides, methods of producing antibodies in laying hens by injecting the peptides, and methods of improving resistance to eggshell breakage and/or increasing eggshell strength by administering an FGF-23 epitope peptide to a laying hen.

6 Claims, 3 Drawing Sheets

Specification includes a Sequence Listing.

FGF-23 EPITOPE PEPTIDE FOR IMPROVING RESISTANCE TO BREAKAGE AND EGGSHELL STRENGTH

CROSS-REFERENCE TO RELATED APPLICATIONS

This application claims priority to U.S. Provisional Application 62/374,224 filed on Aug. 12, 2016, which is incorporated herein by reference in its entirety.

FIELD OF THE DISCLOSURE

The present disclosure is related to compositions and methods for reducing egg breakage and/or by improving the eggshells of eggs laid by laying hens.

BACKGROUND

It has been estimated that the income loss to U.S. producers from broken eggs is $266 million/year based on 240 million laying chickens. An additional loss of $211 million occurs due to uncollectable eggs at processing plants. Today, the U.S. has 338 million laying chickens, and egg loss due to breakage or uncollectable eggs could account for $375 million and $297 million/year, respectively. Global hen numbers are 6.6 billion and could account for losses due to breakage or uncollectable eggs of $7.3 billion and $5.8 billion respectively. With as much as 20% of the eggs lost from a given hen (300 egg/year), a total of $3.50 of an individual hen's production is lost due to egg breakage. The egg specific gravity, percent shell, and force to break the shell (grams of force) are negatively correlated with egg breakage in commercial egg production and packing facilities, with specific gravity and percent shell having a correlation coefficient of ≥0.85 (C. F. Strong, 1989, Poultry Science 68:1730-1733). A strategy that would reduce egg loss due to breakage would be of considerable value to egg producers.

There are no products that are currently marketed that consistently increase egg specific gravity, eggshell amount and force to break eggs (measures of "eggshell strength") and thereby reduce egg breakage. For example, while calcium and vitamin D are two critical nutrients for assuring proper calcification of eggs, these nutrients are currently fed at levels that maximize eggshell strength. Sodium bicarbonate can restore shell strength caused by a depletion of blood bicarbonate when environmental temperatures are high such as in the summer, however, sodium bicarbonate does not actually increase shell strength per se.

What is needed are compositions and methods for reducing breakage and increasing eggshell strength in eggs laid by laying hens.

BRIEF SUMMARY

In an aspect, an FGF-23 epitope peptide has the sequence SEQ ID NO: 3, SEQ ID NO: 4, SEQ ID NO: 5, SEQ ID NO: 6, SEQ ID NO: 7. SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20. In an aspect, the FGF-23 epitope peptide is conjugated to a carrier protein.

In another aspect, a pharmaceutical composition comprises a pharmaceutically acceptable excipient and an FGF-23 epitope peptide, wherein the FGF-23 epitope peptide has the sequence SEQ ID NO: 3, SEQ ID NO: 4, SEQ ID NO: 5, SEQ ID NO: 6, SEQ ID NO: 7. SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20.

In an aspect, a method of improving resistance to eggshell breakage and/or improving eggshell strength comprises administering to a laying hen an effective amount of an FGF-23 epitope peptide to improve resistance to eggshell breakage and/or improve the eggshell strength of eggs laid by the hen, wherein the FGF-23 epitope peptide consists of a sequence that is not identical to a sequence in human FGF-23.

In another aspect, a method of producing antibodies in a laying hen comprises administering to the laying hen an effective amount of an FGF-23 epitope peptide, wherein the FGF-23 epitope peptide has the sequence SEQ ID NO: 3, SEQ ID NO: 4, SEQ ID NO: 5, SEQ ID NO: 6, SEQ ID NO: 7. SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20.

Figure 1:
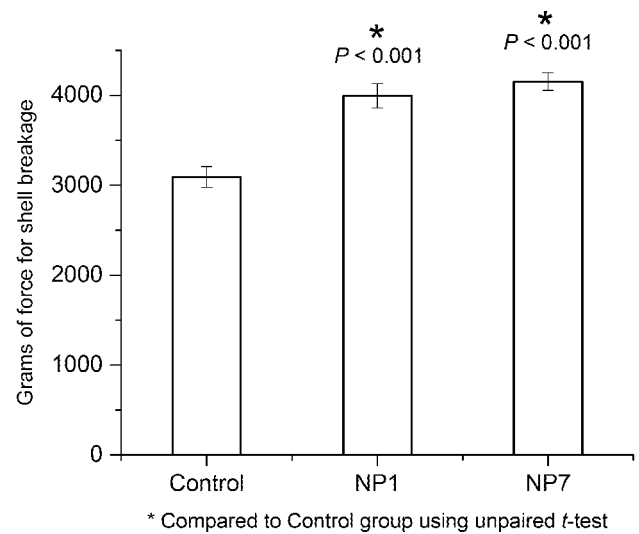
FIG. 1 is a bar graph showing g of force need to break the eggshell for eggs collected from hens injected with control, NP1, or NP7 peptide.
Figure 2:
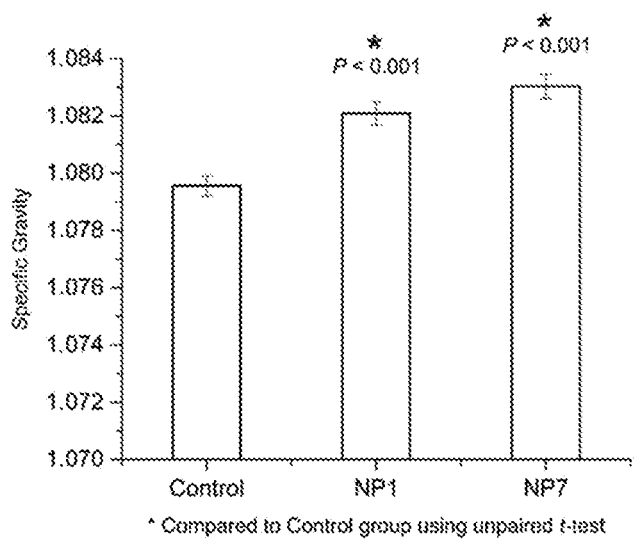
FIG. 2 is a bar graph showing egg specific gravity for eggs collected from hens injected with control, NP1, or NP7 peptide.
Figure 3:
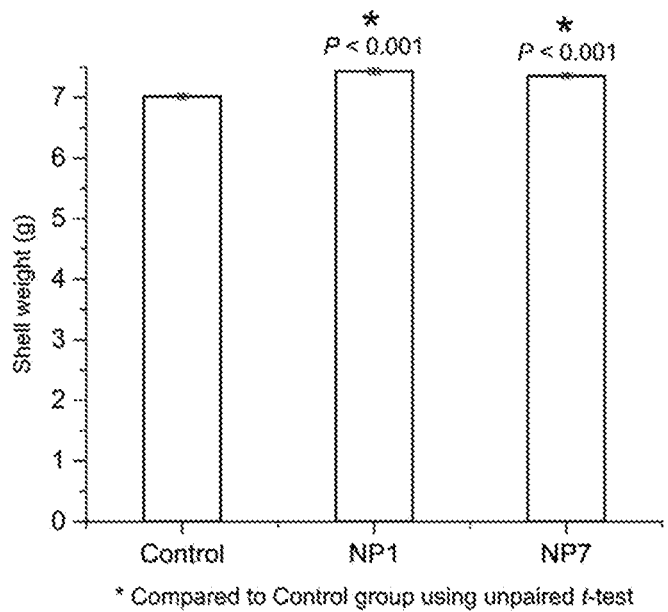
FIG. 3 is a bar graph showing shell weight (g) for eggs collected from hens injected with control, NP1, or NP7 peptide.
Figure 4:
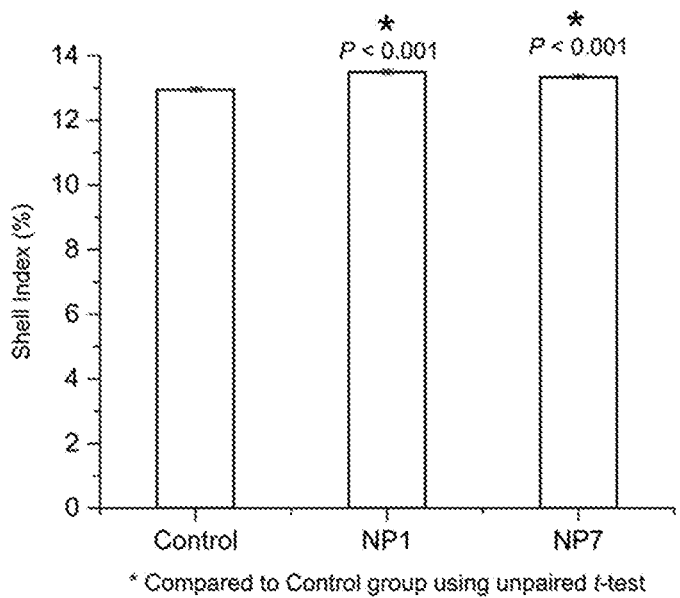
FIG. 4 is a bar graph showing shell index (% of whole egg) for eggs collected from hens injected with control, NP1, or NP7 peptide.

The above-described and other features will be appreciated and understood by those skilled in the art from the following detailed description, drawings, and appended claims.

DETAILED DESCRIPTION

As described in U.S. Pat. No. 9,078,842, hens injected with an FGF-23 epitope peptide have reduced excreta phosphate. In addition, the chicks of these hens have reduced phosphorus deficiency when fed low non-phytate phosphorus diets. During subsequent studies, the present inventors observed that the eggs from hens injected with this FGF-23 epitope peptide were more resistant to breakage than control injected hens. More specifically, eggs from hens injected with FGF-23 epitope peptides GMNPPPYS (NP1; SEQ ID NO: 1) or YTSTERNSFH (NP7; SEQ ID NO: 3) had significantly greater (P<0.001) shell weight, percent shell weight, and specific gravity (a measure of shell quantity) than control injected eggs. Other egg variables such as egg size, internal component content, and dry matter of egg internal components were not consistently affected by vaccine type (FGF-23 epitope peptide or control). For example, to quantify the results, eggs from control and FGF-23 epitope peptide vaccinated hens were subjected to load resistance testing using a Stable Micro System. Eggs from hens vaccinated with either FGF-23 epitope peptide required 30% more force to break the egg (P<0.001) as well as significant increased other measures of shell strength. Thus, the present inventors have unexpectedly found that administration of FGF-23 epitope peptides to laying hens provides eggs with improved resistance to shell breakage and/or improved shell strength, which will increase the number of collectable (i.e., intact) eggs produced by the hens.

In one aspect, a FGF-23 epitope peptide comprises an epitope sequence from avian FGF-23. An FGF-23 epitope peptide does not include a full-length FGF-23 sequence, and typically contains 8-12, more specifically 8-10 amino acid residues. In one embodiment, the avian FGF-23 epitope peptide consists of an epitope that is not found in human FGF-23, such that the antibodies produced upon vaccination of a hen will not cross-react with human FGF-23. The homology of the NP1 and NP7 peptides between human and chicken is shown in Table 1:

TABLE 1

Homology of FGF-23 epitope between chicken and human

|  | NP1 | NP7 |
| --- | --- | --- |
| Human | GMNPPPYS (SEQ ID NO: 1) | YTATARNSYH (SEQ ID NO: 2) |
| Chicken | GMNPPPYS (SEQ ID NO: 1) | YTSTERNSFH (SEQ ID NO: 3) |

Exemplary avian FGF-23 epitope peptides are provided in Table 2:

TABLE 2

Avian FGF-23 epitope sequences

| Peptide | Sequence | Description | SEQ ID NO: |
| --- | --- | --- | --- |
| NP-1 | GMNPPPYS | chicken | 1 |
| NP-7h | YTATARNSYH | human | 2 |
| NP-7 | YTSTERNSFH | chicken, turkey, quail | 3 |
| NP-7D | YTSSERNSFH | duck | 4 |
| ESS-1 | LLNPSWGN | chicken, duck, turkey, quail | 5 |
| ESS-2 | NSSPLLNP | chicken, duck, turkey, quail | 6 |
| ESS-3 | KSEGAGCV | chicken, duck | 7 |
| ESS-3TQ | KSEGAGSV | turkey, quail | 8 |
| ESS-4 | STERNSFH | chicken, turkey, quail | 9 |
| ESS-4D | SSERNSFH | duck | 10 |
| ESS-5 | HINGVPHQ | chicken | 11 |
| ESS-5D | YIDGVPHQ | duck | 12 |
| ESS-5T | HISGVPYQ | turkey | 13 |
| ESS-5Q | HISGVPHQ | quail | 14 |
| ESS-6 | NTPEPHRN | chicken, duck, turkey, quail | 15 |

TABLE 2-continued

Avian FGF-23 epitope sequences

| Peptide | Sequence | Description | SEQ ID NO: |
| --- | --- | --- | --- |
| ESS-7 | VPHQTIYS | chicken, duck, quail | 16 |
| ESS-7T | VPYQTIYS | turkey | 17 |
| ESS-8 | ITGVKSGR | chicken, duck, turkey, quail | 18 |
| ESS-9 | QINADGHI | chicken, turkey, quail | 19 |
| ESS-9D | QINADGYI | duck | 20 |

In one embodiment, the FGF-23 epitope peptide comprises, consists essentially of, or consists of SEQ ID NO: 1, SEQ ID NO: 2, SEQ ID NO: 3, SEQ ID NO: 4, SEQ ID NO: 5, SEQ ID NO: 6, SEQ ID NO: 7. SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20. In another aspect, the FGF-23 epitope peptide comprises, consists essentially of, or consists of SEQ ID NO: 3, SEQ ID NO: 4, SEQ ID NO: 5, SEQ ID NO: 6, SEQ ID NO: 7. SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20.

In one embodiment, the FGF-23 epitope peptide is conjugated to a carrier such as a carrier protein, for example, for formulation into a vaccine. Exemplary carrier proteins include bovine gamma globulin, bovine serum albumin, keyhole limpet hemocyanin, ovalbumin, or a protein that, when conjugated with the peptide, elicits an antibody to the attached peptide.

The epitope peptide may be conjugated (e.g., covalently conjugated) to the carrier protein according to methods known in the art. In some embodiments, the epitope sequence is conjugated to the carrier protein via a glutaraldehyde linking moiety. In other embodiments, the epitope sequence is conjugated to the carrier protein via maleimide mediated conjugation. In some embodiments, the epitope sequence is conjugated via 1-ethyl-3-[3-dimethylaminopropyl]carbodiimide hydrochloride (EDC) mediated conjugation. Other methods of hatpen-carrier protein conjugation may be used and the method of conjugation is not critical as long as antibodies to the desired conjugated peptide may be effectively generated.

Also includes herein are pharmaceutical compositions, such as oral, aerosol and parenteral compositions, and more particularly vaccine compositions, comprising an FGF-23 epitope peptide and a pharmaceutically acceptable carrier.

As used herein, "pharmaceutical composition" means therapeutically effective amounts of the FGF-23 epitope peptide, optionally conjugated to a carrier protein, together with a pharmaceutically acceptable excipient, such as diluents, preservatives, solubilizers, emulsifiers, and adjuvants. As used herein "pharmaceutically acceptable excipients" are well known to those skilled in the art.

In an aspect, the FGF-23 epitope peptide is conjugated to a carrier for aerosol or oral administration. For example, the peptide can be conjugated to a virus or a particle such as a nanoparticle. Alternatively, the peptide can be encoded by a polynucleotide, wherein a sequence encoding the peptide is operably linked to expression control sequences as are known in the art, such that upon administration to a host, the peptide is synthesized, allowing for production of antibodies that neutralize FGF-23 in the host.

For oral administration, a pharmaceutical composition can take the form of, for example, a tablets or a capsule prepared by conventional means with a pharmaceutically acceptable excipient. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives.

Aerosol formulations can be administered via inhalation and can be propellant or non-propellant based. For example, embodiments of the pharmaceutical formulations of the disclosure comprise a peptide of the disclosure formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself (e.g., by an elastic bladder)).

In an aspect, the FGF-23 epitope peptide is administered parenterally in a sterile medium, either subcutaneously, intravenously, intradermally, intraperitoneally, or intramuscularly. Depending on the vehicle and concentration used, the peptide can either be suspended or dissolved in the vehicle. Advantageously, adjuvants such as a local anaesthetic, preservative and buffering agent can be dissolved in the vehicle may also be administered parenterally in a sterile medium, either subcutaneously, or intravenously, or intradermally, or intraperitoneally, or intramuscularly, in the form of sterile injectable aqueous or oleaginous suspensions. Depending on the vehicle and concentration used, the peptide can either be suspended or dissolved in the vehicle. Advantageously, adjuvants such as a local anaesthetic, preservative and buffering agent can be dissolved in the vehicle.

A vaccine composition may comprise an immunopotentiator as the pharmaceutically acceptable excipient, specifically an immunological adjuvant. Exemplary adjuvants include individually or mixtures of alum, aluminum phosphate, aluminum hydroxide, C-phosphae guanosine (CPG), squalene, and oil-based adjuvants including Freund's Complete and Incomplete adjuvant or others as listed in Cooper, P. D. (The selective induction of different immune responses by vaccine adjuvants; Strategies in Vaccine Design. G. L. Ada, ed. R. G. Landes Company, Austin. Tex. (1994)). A specific adjuvant is Freund's complete adjuvant. Another specific adjuvant is Freund's incomplete adjuvant. Branded commercial adjuvants are also available and are suitable such as, for example, TiterMax®, AddaVax™, and Alhydrogel®. Exemplary concentrations of the FGF-23 epitope peptide in an adjuvant formulation generally are about 50 micrograms to about 6 milligrams, specifically about 50 micrograms to about 3 milligrams, even more specifically between about 50 micrograms to about 1 milligram.

In an aspect, a method of producing antibodies in a laying hen comprises administering (e.g., injecting) to the laying hen an effective amount of an FGF-23 epitope peptide, wherein the FGF-23 epitope peptide has the sequence SEQ ID NO: 2, SEQ ID NO: 3, SEQ ID NO: 4, SEQ ID NO: 5, SEQ ID NO: 6, SEQ ID NO: 7. SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20. Exemplary hens include chicken, turkey, duck, goose, peafowl, emu, pheasant, guinea fowl, quail, and the like. Administering the FGF-23 epitope peptide provides FGF-23 neutralizing antibodies, that is, antibodies produced during an immune response in the hen that neutralize FGF-23 that she produces. Since eggs are consumed by humans, in an aspect the antibodies will not neutralized FGF-23 in the consumer of the eggs, since the peptide injected into the chickens is not homologous with the human peptide sequence.

In one aspect, a method of improving resistance to eggshell breakage and/or improving eggshell strength comprises administering (e.g., intramuscular injection) a laying hen with an effective amount of an FGF-23 epitope peptide to improve resistance to eggshell breakage and/or improve eggshell strength. Improving the resistance to breakage and/or eggshell strength will provide improve the number of collectable eggs produced by the hen. In one embodiment, the FGF-23 epitope peptide consists of a sequence that is not identical to a sequence in human FGF-23. In another embodiment, the method comprises injecting a laying hen with a peptide of any one of SEQ ID Nos. 1-20. In another embodiment, the method comprises injecting a laying hen with a peptide of any one of SEQ ID Nos. 3-20. Exemplary hens include chicken, turkey, duck, goose, peafowl, emu, pheasant, guinea fowl, quail, and the like. Injection of the hens with the FGF-23 epitope peptide provides maternal FGF-23 neutralizing antibodies, that is, antibodies produced during an immune response in the hen that inhibit the action of maternal FGF-23.

In an aspect, the laying hen is greater than 35 weeks in age, and administration prevents eggshell deterioration as the laying hen ages.

As used herein, the phrases "improve resistance to eggshell breakage" and "improve eggshell strength" of an egg means that, on average, the grams of force needed to break the egg shell is increased by greater than or equal to 10%, 15%, 20% or more compared to eggs laid by similar hens that are not injected with an FGF-23 epitope peptide. Shell strength can be measured by any one or more of load resistance testing with a 50-kg load cell, 2 mm/s test speed, 0.001 kg trigger force, and a 50 mm diameter cylindrical probe; egg shell specific gravity measured by flotation in sodium chloride and water solutions having sodium chloride concentrations of 1.070, 1.074, 1.078, 1.082, 1.086, 1.090, 1.094, and 1.098M; or shell weight.

According to some methods of the present disclosure, a laying hen is administered a composition comprising an FGF-23 epitope peptide, for example an FGF-23 epitope peptide conjugated to a carrier protein. The composition, e.g., the conjugate vaccine, may be carried in an adjuvant, e.g., Freund's complete adjuvant. In some embodiments, the laying hen may be vaccinated in combination with a conventional vaccination regimen. Administration may occur once or multiple times, e.g., a secondary booster administration about one to two weeks after the primary administration. A secondary booster administration may comprise the same adjuvant or a different adjuvant, e.g., Freund's incomplete adjuvant.

Administration of the peptide elicits an immune system response, which results in the production of antibodies against an endogenous protein, specifically, antibodies against endogenous FGF-23. The laying hen's immune system recognizes the epitopes, which mobilizes the preparation of maternal antibodies that recognize the FGF-23 epitope peptide sequence.

The invention is further illustrated by the following non-limiting examples.

EXAMPLE 1: Effect of Anti-FGF-23 Antibodies on Egg Quality of Laying Hens

Methods

Peptide Conjugation and Hen Vaccination: Two synthetic chicken FGF-23 epitope peptides (NP1, GMNPPPYS (SEQ ID NO: 1); and NP7, YTSTERNSFH (SEQ ID NO: 3); synthesized by GeneScript, Piscataway, N.J.) were individually conjugated to bovine gamma globulin (BgG, Sigma, St. Louis, Mo.) using a glutaraldehyde conjugation procedure. Briefly, 10 mg of BgG and 10 mg peptide were dissolved in 2 mL of 0.1 M sodium acetate buffer (PH=7). 1.3 ml of 2 M glutaraldehyde was then added to the buffer, followed by a 3 hour conjugation period. Peptide conjugation was then stopped by adding 100 mg glycine in the reaction system for 1 hour. The conjugation solution was dialyzed against PBS (PH=7) overnight in dialysis bag with a cutoff molecular weight of 6000-8000. For primary vaccination, FGF-23 epitope peptide-BgG conjugates (dialysate) were prepared as vaccines using Freund's Complete Adjuvant as the adjuvant and intramuscularly injected (breast and thigh muscle) into 30 Single Comb White Leghorn laying hens (15 hens for NP1-BgG conjugate, and 15 hens for NP7-BgG conjugate). For booster injections, FGF-23 peptide-BgG conjugates (dialysate) were prepared as vaccines using Freund's Incomplete Adjuvant as the adjuvant. Four booster injections were given after 2 weeks, 4 weeks, 24 weeks and 44 weeks following the primary injection to maintain antibody levels. Another 14 hens were injected with unconjugated BgG (no peptide conjugate) using the same time points and adjuvants as described for the FGF-23 epitope peptide and served as the control vaccinated hens. All the hens used were individually housed in cages with raised wire floors and maintained under a 16-hour light: 8-hour dark lighting regimen with free access to feed and water.

Sample Collection: Eggs were collected for 20 consecutive days after 1 week following the fourth booster injection. Egg weight (g), specific gravity (see below for analysis details), shell weight (g), yolk weight (g), albumen weight (g), dry matter content of the whole egg (%), dry matter content of the shell (%), dry matter content of the yolk (%), and dry matter content of the albumen (%) were determined. Also calculated were shell index (shell weight/egg weight×100%), yolk index (yolk weight/egg weight×100%), albumen index (albumen weight/egg weight×100%), the percent of shell dry matter in whole egg dry matter (%), the percent of yolk dry matter in whole egg dry matter (%), the percent of albumen dry matter in whole egg dry matter (%), and the yolk to albumen ratio (yolk weight:albumen weight, g:g) were calculated.

Egg specific Gravity: Solutions containing sodium chloride and water were created with molarity concentrations of 1.070, 1.074, 1.078, 1.082, 1.086, 1.090, 1.094, and 1.098 at volumes of 1000 mL. The eggs were individually tested starting from lowest molarity to highest molarity, with the molarity in which the egg began floating recorded for the specific gravity measurement.

Egg Shell Strength: For shell strength determination, eggs were collected for 5 consecutive days after 4 weeks following the fourth booster injection. Shell strength was determined using a TA.HDPlus Texture Analyzer (Stable Micro Systems, Texture Technologies Corp., South Hamilton, Mass.) and Texture Expert software (Exponent Lite 6,1,4,0). Shell strength determinations were conducted utilizing a 50-kg load cell, 5 mm/s pre-test speed, 2 mm/s test speed, 0.001 kg trigger force, 50 mm diameter aluminum cylindrical probe (P/50), and egg holder (diameter 32 mm, height 27 mm, plastic cap).

Results

Hens were vaccinated with either Control (FCA, n=15), NP1 peptide (GMNPPPYS, n=15, SEQ ID NO: 1), or NP7 peptide (YTSTERNSFH, n=15; SEQ ID NO: 2). Eggs were collected during peak antibody production (within 2 months after booster vaccination, when hens were 69 to 72 weeks of age).

TABLE 3

Effect of anti-FGF-23 antibodies on egg quality of 69- to 71-wk-old laying hens

|  | FCA | | NP1 | | NP7 | | P-value (independent t-test) | |
| --- | --- | --- | --- | --- | --- | --- | --- | --- |
|  | mean | SE | mean | SE | mean | SE | FCA&NP1 | FCA&NP7 |
| Shell Strength (g of force) | 3093 | 117 | 3995 | 135 | 4153 | 99 | <0.001 | <0.001 |
| Specific Gravity | 1.080 | 0.0004 | 1.082 | 0.0004 | 1.083 | 0.0004 | <0.001 | <0.001 |
| Shell Weight (g) | 7.02 | 0.04 | 7.43 | 0.05 | 7.36 | 0.04 | <0.001 | <0.001 |
| Shell Index (%) | 12.95 | 0.07 | 13.49 | 0.07 | 13.34 | 0.07 | <0.001 | <0.001 |
| Egg Weight (g) | 54.25 | 0.26 | 55.16 | 0.26 | 55.30 | 0.30 | 0.014 | 0.080 |
| Yolk Weight (g) | 17.38 | 0.10 | 17.72 | 0.09 | 17.37 | 0.12 | 0.014 | 0.912 |
| Yolk Index (%) | 32.08 | 0.16 | 32.19 | 0.15 | 31.46 | 0.19 | 0.623 | 0.011 |
| Albumen Weight (g) | 29.30 | 0.21 | 29.46 | 0.22 | 31.46 | 0.24 | 0.595 | 0.035 |
| Albumen Index (%) | 53.94 | 0.22 | 53.31 | 0.23 | 54.12 | 0.24 | 0.050 | 0.583 |
| Total Egg DM (%) | 35.72 | 1.57 | 35.77 | 1.26 | 35.22 | 0.74 | 0.981 | 0.772 |
| Yolk DM (%) | 19.90 | 2.71 | 22.12 | 2.76 | 19.28 | 2.58 | 0.571 | 0.869 |
| Shell DM (%) | 74.00 | 1.18 | 75.47 | 1.96 | 75.13 | 2.71 | 0.526 | 0.705 |
| Albumen DM (%) | 47.06 | 3.88 | 42.83 | 3.61 | 47.21 | 3.63 | 0.430 | 0.978 |
| Yolk DM Percent in Total Egg DM (%) | 27.55 | 2.63 | 30.42 | 2.91 | 27.70 | 2.82 | 0.470 | 0.970 |
| Shell DM Percent in Total Egg DM (%) | 28.64 | 0.92 | 29.12 | 0.74 | 29.41 | 0.53 | 0.685 | 0.475 |
| Albumen DM Percent in Total Egg DM (%) | 43.80 | 2.47 | 40.46 | 2.72 | 42.89 | 2.75 | 0.370 | 0.806 |
| Yolk to Albumen Ratio (g/g) | 0.60 | 0.01 | 0.61 | 0.01 | 0.59 | 0.01 | 0.206 | 0.189 |

As shown in FIGS. 1-4, the egg shell strength, measured as g of force, specific gravity of the eggs, shell weight in g and shell index, increased after injection of either NP1 or NP7 FGF-23 epitope peptide (when hens were 72-wk-old). Table 1 demonstrates that the presence of antibody to FGF-23 had no adverse effects on any measure of internal quality; hence eggshell strength could be increased without adversely affecting internal or edible egg quality. The slight increase in egg weight in eggs from hens injected with an FGF-23 peptide was likely due to the significant increase in eggshell weight. All other changes in internal egg measurements were not consistent across the FGF-23 peptides used. Most important is that yolk and albumen dry matter were not adversely affected by the use of FGF-23 peptide immunizations. Maintenance of dry matter is important to egg breaking operations which want to maintain solids levels for egg drying. The finding that a peptide (e.g., NP7) was as effective as NP1 in inducing maternal antibodies that increased shell strength was important. NP1 has sequence homology to human FGF-23. Antibodies made the NP1 could possibly bind human FGF-23 if the egg containing the antibody was consumed by humans intact (not denatured through cooking) and the hormone was present in the gastrointestinal tract lumen (FGF-23 has not been shown to be present in the gastrointestinal tract lumen or to have any biological role in the gastrointestinal tract lumen). The potential cross reactivity of FGF-23 NP1 antibody to human FGF-23 could be viewed as a potential food safety issue. However NP7, which is much less homologous to the sequence in humans (3 nonmatching amino acids), suggest that antibody to chicken FGF-23 (NP7) is less likely to cross react with human FGF-23.

EXAMPLE 2: Effect of Anti-FGF-23 Antibodies on Egg Quality of Young Laying Hens

Hens were vaccinated with either control or FGF-23 peptide vaccines at the age of 26 weeks. Two booster injections were conducted 2 and 4 wk after the primary injection. Hens were at peak antibody titer 1 wk after the second booster injection. Eggs were collected for 28 consecutive days beginning when hens were at 31 weeks of age and when the antibody was at maximum levels. Shell strength (the peak force value at shell breakage) was determined using a TA.HDPlus Texture Analyzer (Stable Micro Systems, Texture Technologies Corp., South Hamilton, Mass.) with Texture Expert software (Exponent Lite 6,1,4,0) at the University of Wisconsin-Madison Meat Science & Muscle Biology Laboratory. Shell strength determinations were conducted utilizing a 50-kg load cell with 5 mm/s pre-test speed, 2 mm/s test speed, 15 mm test distance, 0.001 kg trigger force, a 50-mm diameter aluminum cylindrical probe (P/50), and an egg holder (diameter 32 mm, height 27 mm, plastic cap, eggs were positioned blunt end up).

TABLE 4

Egg shell strength of FGF-23 vaccinated young laying hens (from 31 to 35 wk of age)

| Treatment | SEQ ID NO: | Number of eggs | Shell Strength (g of force) | SE | P-value* |
|---|---|---|---|---|---|
| Control |  | 99 | 4822 | 65 | — |
| NP1 | 1 | 97 | 4632 | 66 | 0.041 |
| ESS1 | 5 | 103 | 4799 | 82 | 0.832 |
| ESS2 | 6 | 91 | 4765 | 72 | 0.559 |
| ESS3 | 7 | 87 | 4380 | 73 | <0.001 |

TABLE 4-continued

Egg shell strength of FGF-23 vaccinated young laying hens (from 31 to 35 wk of age)

| Treatment | SEQ ID NO: | Number of eggs | Shell Strength (g of force) | SE | P-value* |
|---|---|---|---|---|---|
| ESS4 | 9 | 78 | 4322 | 72 | <0.001 |
| ESS5 | 11 | 96 | 4415 | 77 | <0.001 |
| ESS6 | 15 | 44 | 4762 | 121 | 0.635 |
| ESS7 | 16 | 89 | 4281 | 73 | <0.001 |
| ESS8 | 18 | 97 | 4732 | 78 | 0.379 |
| ESS9 | 19 | 97 | 4582 | 72 | 0.014 |

*Two tailed independent t-test against to the control group.

As shown in Table 4, from this trial it was concluded that the FGF-23 vaccine did not improve eggshell strength in the young (less than 35 weeks of age) hens, while the FGF-23 vaccine did improve eggshell strength in the older hens. It is well known that young hens produce smaller eggs with the same amount of eggshell (calcium carbonate) as older hens. As the hen gets older the egg size increases and the egg shell is thinned to cover the same amount of surface area as the eggs from the older hens. The FGF-23 vaccine appears to protect egg shell deterioration with hen aging.

EXAMPLE 3: Effect of Anti-FGF-23 Antibodies on Egg Quality of Young and Old Laying Hens Young (n=20, 32-wk-old) and old (n=20, 71-wk-old) laying hens were injected with either a control vaccine or FGF-23 peptide NP-7 vaccine (see Table 5). Two booster injections were conducted 2 and 4 wk after the primary injection. Hens were at peak antibody titer 1 wk after the second booster injection. The eggs were collected for 5 consecutive days (hens were 37 and 76 wk of age, respectively). Shell strength of the eggs were analyzed at UW-Meat Science & Muscle Biology Laboratory. Blood samples of these hens will be collected and analyzed for calcium, phosphate, FGF-23 and $1,25(OH)_2D_3$ levels.

TABLE 5

Experimental design

| Hens | Vaccine |
|---|---|
| 32-wk-old | Control (n = 10) |
|  | NP-7 (n = 10) |
| 71-wk-old | Control (n = 10) |
|  | NP-7 (n = 10) |

Figure 5:
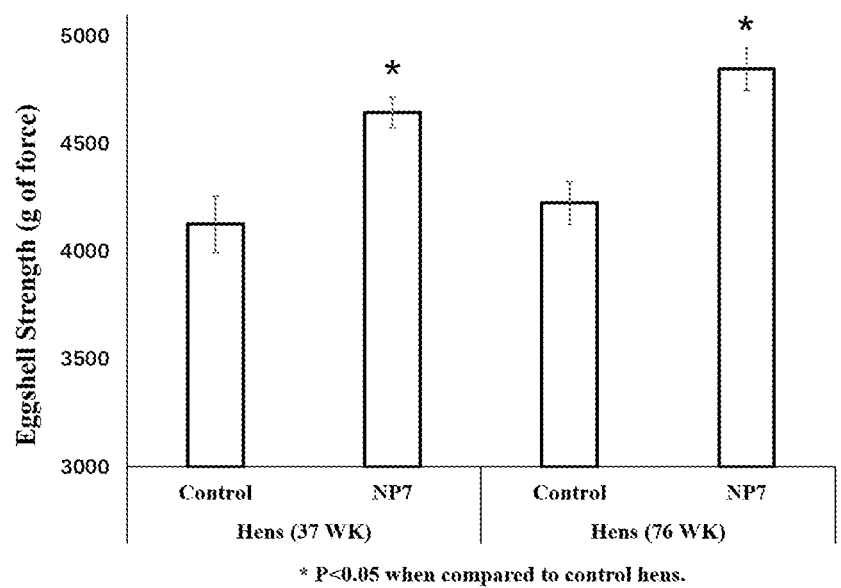
FIG. 5 shows eggshell strength in g of force for eggs from 37 and 76 week old hens treated with control or NP7 peptide.

As shown on FIG. 5. FGF-23 peptide NP-7 vaccine increased eggshell strength of eggs from 37- and 76-wk-old laying hens. These anticipated results may be explained by plasma levels of phosphate, calcium, FGF-23 and $1,25(OH)_2D_3$.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An FGF-23 epitope peptide, wherein the peptide is 8-12 amino acids in length and comprises SEQ ID NO: 3 or SEQ ID NO: 4 and wherein the FGF-23 epitope peptide is conjugated to a carrier protein.

2. The FGF-23 epitope peptide of claim 1, wherein the carrier protein is bovine gamma globulin, bovine serum albumin, keyhole limpet hemocyanin, or ovalbumin.

3. A pharmaceutical composition comprising a pharmaceutically acceptable excipient and an FGF-23 epitope peptide, wherein the FGF-23 epitope peptide is 8-12 amino acids in length and comprises SEQ ID NO: 3 or SEQ ID NO: 4, and wherein the FGF-23 epitope peptide is conjugated to a carrier protein.

4. The composition of claim 3, wherein the carrier protein is bovine gamma globulin, bovine serum albumin, keyhole limpet hemocyanin, or ovalbumin.

5. The pharmaceutical composition of claim 3, wherein the composition is for oral, aerosol, or parenteral administration.

6. The pharmaceutical composition of claim 5, wherein the pharmaceutically acceptable excipient is an immunological adjuvant.

* * * * *

```
                         SEQUENCE LISTING

<160> NUMBER OF SEQ ID NOS: 20

<210> SEQ ID NO 1
<211> LENGTH: 8
<212> TYPE: PRT
<213> ORGANISM: gallus gallus

<400> SEQUENCE: 1

Gly Met Asn Pro Pro Pro Tyr Ser
1               5

<210> SEQ ID NO 2
<211> LENGTH: 10
<212> TYPE: PRT
<213> ORGANISM: homo sapiens

<400> SEQUENCE: 2

Tyr Thr Ala Thr Ala Arg Asn Ser Tyr His
1               5                   10

<210> SEQ ID NO 3
<211> LENGTH: 10
<212> TYPE: PRT
<213> ORGANISM: gallus gallus

<400> SEQUENCE: 3

Tyr Thr Ser Thr Glu Arg Asn Ser Phe His
1               5                   10

<210> SEQ ID NO 4
<211> LENGTH: 10
<212> TYPE: PRT
<213> ORGANISM: Anas

<400> SEQUENCE: 4

Tyr Thr Ser Ser Glu Arg Asn Ser Phe His
1               5                   10

<210> SEQ ID NO 5
<211> LENGTH: 8
<212> TYPE: PRT
<213> ORGANISM: gallus gallus

<400> SEQUENCE: 5

Leu Leu Asn Pro Ser Trp Gly Asn
1               5
```

-continued

```
<210> SEQ ID NO 6
<211> LENGTH: 8
<212> TYPE: PRT
<213> ORGANISM: gallus gallus

<400> SEQUENCE: 6

Asn Ser Ser Pro Leu Leu Asn Pro
1               5

<210> SEQ ID NO 7
<211> LENGTH: 8
<212> TYPE: PRT
<213> ORGANISM: gallus gallus

<400> SEQUENCE: 7

Lys Ser Glu Gly Ala Gly Cys Val
1               5

<210> SEQ ID NO 8
<211> LENGTH: 8
<212> TYPE: PRT
<213> ORGANISM: Meleagris gallopavo

<400> SEQUENCE: 8

Lys Ser Glu Gly Ala Gly Ser Val
1               5

<210> SEQ ID NO 9
<211> LENGTH: 8
<212> TYPE: PRT
<213> ORGANISM: gallus gallus

<400> SEQUENCE: 9

Ser Thr Glu Arg Asn Ser Phe His
1               5

<210> SEQ ID NO 10
<211> LENGTH: 8
<212> TYPE: PRT
<213> ORGANISM: anas

<400> SEQUENCE: 10

Ser Ser Glu Arg Asn Ser Phe His
1               5

<210> SEQ ID NO 11
<211> LENGTH: 8
<212> TYPE: PRT
<213> ORGANISM: gallus gallus

<400> SEQUENCE: 11

His Ile Asn Gly Val Pro His Gln
1               5

<210> SEQ ID NO 12
<211> LENGTH: 8
<212> TYPE: PRT
<213> ORGANISM: anas

<400> SEQUENCE: 12

Tyr Ile Asp Gly Val Pro His Gln
1               5
```

```
<210> SEQ ID NO 13
<211> LENGTH: 8
<212> TYPE: PRT
<213> ORGANISM: Meleagris gallopavo

<400> SEQUENCE: 13

His Ile Ser Gly Val Pro Tyr Gln
1               5

<210> SEQ ID NO 14
<211> LENGTH: 8
<212> TYPE: PRT
<213> ORGANISM: Coturnix Coturnix

<400> SEQUENCE: 14

His Ile Ser Gly Val Pro His Gln
1               5

<210> SEQ ID NO 15
<211> LENGTH: 8
<212> TYPE: PRT
<213> ORGANISM: gallus gallus

<400> SEQUENCE: 15

Asn Thr Pro Glu Pro His Arg Asn
1               5

<210> SEQ ID NO 16
<211> LENGTH: 8
<212> TYPE: PRT
<213> ORGANISM: gallus gallus

<400> SEQUENCE: 16

Val Pro His Gln Thr Ile Tyr Ser
1               5

<210> SEQ ID NO 17
<211> LENGTH: 8
<212> TYPE: PRT
<213> ORGANISM: Meleagris gallopavo

<400> SEQUENCE: 17

Val Pro Tyr Gln Thr Ile Tyr Ser
1               5

<210> SEQ ID NO 18
<211> LENGTH: 8
<212> TYPE: PRT
<213> ORGANISM: gallus gallus

<400> SEQUENCE: 18

Ile Thr Gly Val Lys Ser Gly Arg
1               5

<210> SEQ ID NO 19
<211> LENGTH: 8
<212> TYPE: PRT
<213> ORGANISM: gallus gallus

<400> SEQUENCE: 19

Gln Ile Asn Ala Asp Gly His Ile
1               5
```

```
<210> SEQ ID NO 20
<211> LENGTH: 8
<212> TYPE: PRT
<213> ORGANISM: anas

<400> SEQUENCE: 20

Gln Ile Asn Ala Asp Gly Tyr Ile
1               5
```